United States Patent
Ting

(10) Patent No.: US 10,152,573 B2
(45) Date of Patent: Dec. 11, 2018

(54) SYSTEM AND METHODS FOR OPTIMIZING COSTS BASED ON CARE PLANS

(71) Applicant: Annsheng Ting, Los Altos Hills, CA (US)

(72) Inventor: Annsheng Ting, Los Altos Hills, CA (US)

(73) Assignee: Annsheng Chien Tng, Los Altos Hills, CA (US)

( * ) Notice: Subject to any disclaimer, the term of this patent is extended or adjusted under 35 U.S.C. 154(b) by 63 days.

(21) Appl. No.: 15/338,502

(22) Filed: Oct. 31, 2016

(65) Prior Publication Data

US 2017/0124267 A1    May 4, 2017

Related U.S. Application Data

(60) Provisional application No. 62/285,450, filed on Oct. 30, 2015.

(51) Int. Cl.
*G06Q 10/06* (2012.01)
*G06F 19/00* (2018.01)

(52) U.S. Cl.
CPC ............ *G06F 19/328* (2013.01); *G06F 19/00* (2013.01); *G06Q 10/06* (2013.01); *G06Q 10/06315* (2013.01); *G06Q 10/063118* (2013.01)

(58) Field of Classification Search
CPC .................................................. G16H 20/10
See application file for complete search history.

(56) References Cited

U.S. PATENT DOCUMENTS

| | | | | |
|---|---|---|---|---|
| 6,434,531 | B1* | 8/2002 | Lancelot | G06F 19/325 705/3 |
| 2002/0128879 | A1* | 9/2002 | Spears | G06Q 30/02 705/4 |
| 2003/0130866 | A1* | 7/2003 | Turner | G06Q 10/10 705/2 |
| 2013/0191159 | A1* | 7/2013 | Camacho | G06F 19/34 705/3 |
| 2014/0207486 | A1* | 7/2014 | Carty | G06Q 50/22 705/2 |
| 2015/0019252 | A1* | 1/2015 | Dawson | A61C 8/00 705/3 |
| 2016/0034668 | A1* | 2/2016 | Rourke | G06F 19/3456 705/2 |
| 2016/0085937 | A1* | 3/2016 | Dettinger | G06F 19/3456 705/2 |

(Continued)

*Primary Examiner* — Daniel J Colilla

(57) ABSTRACT

A system enables users to customize a "total care plan", which consists of a set of in-home care tasks plus additional caregiving related attributes such as time for carrying out a task, supplies needed, and estimated cost for each task. In this system, total care plans are used to plan, schedule and manage a person's daily life for elderly or people with long-term health issues. The included methods provide users ways to optimize the cost of products and services needed to carry out their care plan that meet their quality and financial requirements, and caregiving or health constraints. Methods are provided to further reduce the total cost of the products or services by leveraging the resources they already have, and applying their insurances or social benefits. Methods that offer users the option of applying various ways to get volume discounts are also provided which further optimize costs.

20 Claims, 6 Drawing Sheets

(56) References Cited

U.S. PATENT DOCUMENTS

| | | | |
|---|---|---|---|
| 2016/0098538 A1* | 4/2016 | Dettinger | G06Q 10/10 600/515 |
| 2017/0323398 A1* | 11/2017 | Dintenfass | G06Q 40/06 |
| 2018/0089385 A1* | 3/2018 | Gupta | G06F 19/345 |

* cited by examiner

Example of user interface for viewing a total care plan

Figure 1

SYSTEM AND METHODS FOR OPTIMIZING COSTS BASED ON CARE PLANS

This application claims priority under 35 USC 119(e) and 120 to U.S. Provisional Patent Application Ser. No. 62/285,450 filed on Oct. 30, 2015 and entitled "System and method for optimizing the cost of purchasing of products and services based on medical or non-medical care plans" the entirety of which is incorporated herein by reference.

FIELD OF THE INVENTION

This invention pertains to a system and method for managing an in-home care plan, specifically to a system and method for optimizing the cost of purchasing of products and service resources based on the medical or non-medical in-home care plan.

BACKGROUND OF THE INVENTION

Rapidly growing population of the elderly population is testing the reality of assisted living and nursing home options and the affordability of high costs and complex services. The focus of senior care is significantly shifting toward in-home care. That puts a tremendous burden on the family caregivers.

Almost all family caregivers are not trained in caregiving, and 70% are still in the workforce. They are constantly under stress because they have to visit many websites on the Internet to seek resources including advices, information, professional caregivers, equipment, tools, and supplies. What they found from one site were not recorded for when they find something else from another site later. These untrained caregivers are overwhelmed and desperately want an integrated solution to help them navigate the complexities in finding resources, understanding the coverage from insurance and government social programs, and putting together their own in-home care plan and team with much less stress, time, frustration, and cost while still maintaining the quality of care.

Most existing caregiving solutions today are segregated and with neither a systematic way of allowing caregivers to effectively access caregiving information or create a customized care plan with all resources included in the plan, nor a way to periodically acquire the exact resources needed by the plan while the caregiving is taking place. Furthermore, these solutions only help the complicated caregiving process in a very limited fashion without any way to optimize the financial and quality goal of the care. As such they create more stress, time, as well as increase the cost of the care. A survey with family caregivers (family, relatives, and close friends of the care recipients) found that people demand a solution that help them find a way to optimize the cost of acquiring resources while still provide a quality care.

SUMMARY OF THE INVENTION

The term "template" is used to refer to a generic healthcare treatment plan, protocol, or guideline. After a template has been assigned to a general patient or client, the template is referred to as "plan". This invention provides a set of tools for users to find and customize in-home care plans and then acquire the resources it takes to carry out these plans for an indefinitely period of time. The acquisition of the resources must also meet the financial, quality, and timing requirements of the care recipient, the person who is been treated according to the care plan.

The foundation for the system is to provide a method for people to create a customized and actionable "total care plan" from a curated collection of in-home care information shared by family caregivers who have been in a similar situation and experts who have been working on in-home care plans. A total care plan is a particular form of an in-home care plan defined by the invention. It comprises a series of in-home non-medical caregiving tasks, with required resources, costs, and time commitments associated with each task. It is stored in an object database with special relationships based on the system design. A total care plan template is a total care plan that is curated by the administrator of the system and stored in the Total Careplan database. It is displayed like a Total Care Plan to be displayed by all users but can only be modified by a system administrator. The method is provided with User Interfaces to enable people to create a plan by adopt a template from the curated templates, customize if they wish and carry out the plan when taking care a person who needs care. The user who created a plan is the owner of the plan. A plan can only be accessed, displayed and modified by the owner of the plan. When carrying out the plan, a list of equipment, supplies, and products that are used in carrying out each task by a caregiver team is produced. This list defines a particular total care plan based care package for the care taking. A care process that any caregiver uses to take care of the care recipient is defined by the chosen total care plan plus one of these customized and curated care packages.

According to an exemplary embodiment of the present invention, a system for optimizing the cost of purchasing of products and services based on care plans comprises a total care plan management module for defining and displaying the details included in a total care plan template, providing care plan templates for a user to create his/her customized total care plan, storing the templates and the customized total care plan in a total care plan database, a user and team management module for managing user accounts and their associations with in-home care teams in a users database, wherein the user accounts comprises user specific information and user identity related information, a care resources management module for managing a plurality of care resources included in a care resources database and monitoring whether a change has been made to the care resources, a care package associated with the at least one customized total care plan, wherein a care package is defined as all the care resources required for carrying out the customized total care plan, and a marketplace management module for managing a list of providers of the care resources stored in the care resources database, the care packages needed to be acquired at any point in time, the available care packages that can be used in the total care plans for every user who has a customized plan, and the costs of the care packages, wherein all the activities made by the users accessing the market management module are stored in a marketplace database. These modules work closely to continuously watch out for ways to optimize costs. For example, the care resources management module notifies the market management module when it detects a change has been made to a care package associated with a customized total care plan for the marketplace management module to access external websites and retrieve the latest information related to the care package. With the latest information, the estimated cost of an impacted customized total care plan can be optimized again according to the user preferences. The marketplace management module will also monitor the external product vendor websites for the resources that the total care plan uses. According to the existing users' wish to share excessive products and do appropriate cost related changes, the marketplace management module interacting with the resources management module will adjust the care resources database accordingly and notify the total care plan management to make the necessary changes to its associated care package.

According to an exemplary embodiment of the present invention, the total care plan management module provides a curator interface allowing a system administrator to review and curate a customized total care plan into a curated total care plan template. The new curated total care plan template is then stored in the total care plan database and added to the set of care plan templates that are enabled for sharing with other users.

According to an exemplary embodiment of the present invention, the system further provides a service registration function allowing users to provide a list of available services and excess resources, and a list of services and resources currently in need. When these lists get an update, the marketplace module matches at least one user who needs these services or resources and notifies the matched users of this match.

According to an exemplary embodiment of the present invention, the marketplace management module regularly monitors the external websites of product vendors and social welfare programs or insurance programs, the external systems, and the list of excess resources for automatically updating the total estimated costs for each care plan templates. If it detects changes related to the users and their customized total care plans, it will re-calculate the total costs and inform users that the use of some care resources may change. The care resources management module monitors if a resource in the list of available resources is redundant and prompts the user to register the resource into a sharing pool so the available resource can be re-sold or exchanged for other available resources in the sharing pool and possibly reduce the total cost for the care.

According to an exemplary embodiment of the present invention, a method for optimizing costs based on care plans comprises the following steps: providing a plurality of total care plan templates; allowing users to visually view the details including resource needs of the total care plan templates; defining his/her customized total care plan visually using the total care plan template provided; managing user accounts in a database; monitoring whether a change has been made to the customized total care plan; and managing the total estimated costs and the available resources according to the customized total care plan; wherein when a change has been made to the customized total care plan, latest information is retrieved from external websites and the available resources to optimize the total cost based on user preferences.

According to an exemplary embodiment of the present invention, the method further comprises steps of providing a curator interface for a system administrator to review and curate the customized total care plan into a curated total care plan template, storing the curated total care plan template in the database, appending the curated total care plan template to the set of curated total care plan templates that users can view; and sharing the curated total care plan with other users.

According to an exemplary embodiment of the present invention, the method further comprises steps of providing a service registration function, a list of available services and excess resources from the users, obtaining a list of available services and excess resources from the users, updating a list of needed services and resources from the users requesting for human resources or products, matching at least one service or product in the list of available services and excess resources with at least one in the list of needed services and resources, generating a plurality of suggestion messages, notifying the matched users for possible acquisitions or exchanges, and assigning a user who had agreements with the matched at least one in the list of needed services and resources as a care plan team member of the matched at least one user requesting resources in the list of needed services and resources.

According to an exemplary embodiment of the present invention, the method further comprises steps of monitoring the external websites, external systems, and registered services and products regularly for price changes; and updating the estimated costs for each total care plan templates and every customized total care plan automatically when a price of an element associated with the customized total care plan changed.

According to an exemplary embodiment of the present invention, the method further comprises steps of associating the profile of the user with social welfare programs and insurance programs that the user is qualified for, monitoring external insurance benefits websites and social program benefit websites for changes related to the users with at least one customized care plan for possible optimizing costs or the use of resources of the care plan. When an available resource is redundant, prompting the user to register the available resource into a sharing pool for exchanging for other resources and subsequently reduce cost.

According to an exemplary embodiment of the present invention, the method further comprises steps of monitoring levels of consumption of the consumable resources associated with the customized total care plan; providing options for automatically placing orders or prompting the user to place orders for the consumables; and providing an negotiation interface allowing the plurality of users to negotiate the price for selling and purchasing the consumables from each other.

According to an exemplary embodiment of the present invention, the method further comprises steps of matching the users that use the same consumables in their customized total care plans; sending requests to the matched users to obtain authorization for joining orders for volume discounts; receiving authorization from the matched users; recalculating the estimated cost of each customized total care plan that benefit from the volume discount; and placing orders for the matched users.

According to an exemplary embodiment of the present invention, a computer-readable medium having computer-readable instructions stored thereon that are executed by a processor to perform any one of the exemplary embodiment described above is provided.

BRIEF DESCRIPTION OF THE DRAWINGS

In the drawings, like reference characters generally refer to the same parts throughout the different views. The drawings are not necessarily to scale, instead, emphasis generally being placed upon illustrating the principles of the invention. The dimensions of the various features or elements may be arbitrarily expanded or reduced for clarity. In the following description, various embodiments of the invention are described with reference to the following drawings, in which:

FIG. 1 shows an exemplar user interface of an instance of a "one-stop shop" view for a total care plan or total care plan template;

DETAILED DESCRIPTION OF A PREFERRED EMBODIMENT

The invention is particularly applicable to the consumers who decide to have long term care at home but with limited financial support as well as limited resources including human resources to be utilized by them. The system described here can be referred as CareXc. The system first provides a way to have a customized and actionable "total care plan" from a curated collection of in-home care information shared by family caregivers who have been in similar situations—for example, with loved ones who have similar long term care health conditions and experts who are working in this subject. The definition of a total care plan is part of the present system invention. It has the following specific required content such as in-home non-medical caregiving tasks, for example, give bath (these are tasks can be performed by non-medical certified individuals), required resources, for example diapers, costs of each task, and the amount of time requirements associated with each task. It is with this definition of a care plan, this invention will be described. The data of the total care plan including the care plan itself is stored in the database when it is not being used and the database can be in the cloud implemented in a distributed fashion. The system provides a "one-stop-shop" view created for displaying a total care plan.

Figure 1:
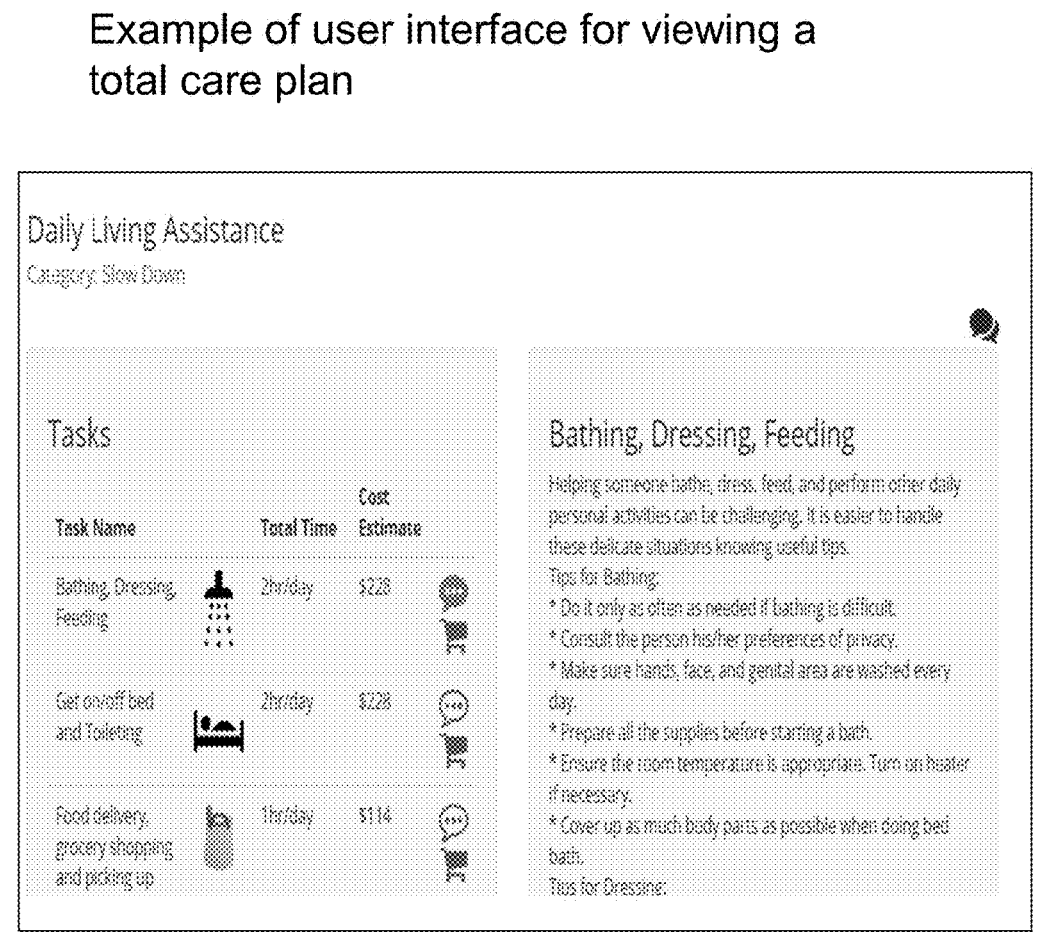

FIG. 1 shows an exemplary user interface that provides the view for users to see all different components that are included in the plan as well as additional external data that are linked to by the plan at one glance. When optimizing the cost of a plan, the optimization method is based on three user modifiable options classes: first options class is tasks, the human resources and product resources in the adopted total care plan and required by the user to carry out the plan; the second options class is the financial profile of the user or related care recipient such as insurances carried; and the third options class is the preferences of the user such as the brand of the product, new or used, cost range, and payment methods. Each options class can be and most likely will be changed by the user periodically, but how frequent each class is changed when time moves on is different. Depending on its frequency, different tools are provided with user interface for users to change these options.

Figure 2:
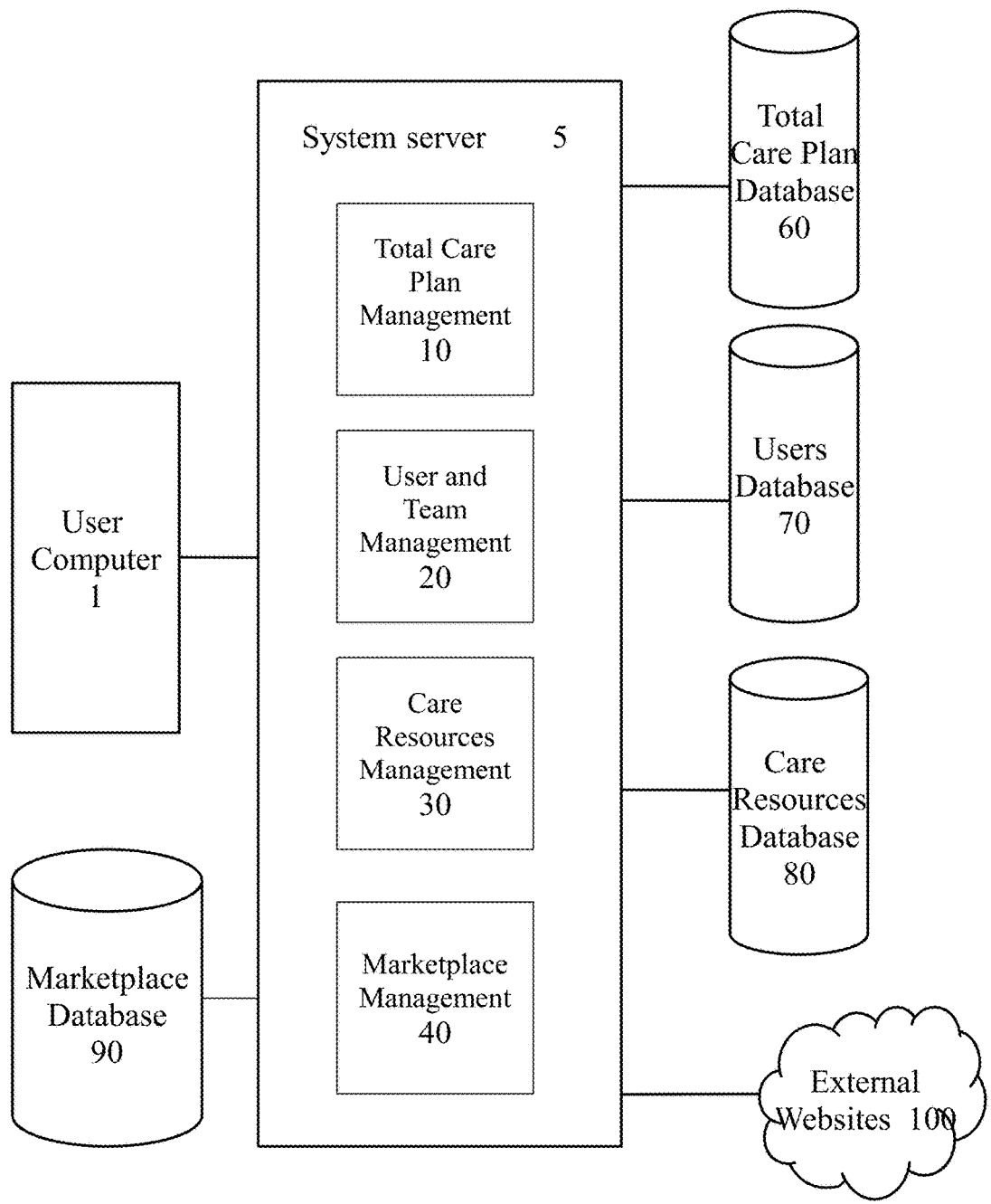
FIG. 2 illustrates the major system components of the present invention, the related databases, and their relationships.

FIG. 2 shows the major system components of the present invention, the related databases, and their relationships. The task options class change is managed as part of the total care plan management module 10, the financial profile options class change is managed by the user and team management module 20, and the resource preference change is managed by the care resources management module 30. The marketplace management module 40 manages all operating activities related to managing the marketplace for example; all different payments accepted by vendors, per vendor volume discount requirements and policy, general policy of the product quality for products to be shared, other general policy such as return goods. By interacting with the other three modules in FIG. 2, the marketplace module also manages the activities related to users using the marketplace.

Contained in each total care plan, there is a list of products that one needs to acquire. This list describes the content of this user's curated care package associated with the total care plan. The cost for carrying out the total care plan contains both the labor cost as listed in the total care plan and the cost of acquiring the care package. The market price for acquiring the care package can be from a combination of the regular vendor price, or used goods price, or can be zero because they are exchanged with other services or products in the system. The cost optimization method collects the various costs associated with each item in the care package from the various ways one can acquire the package and provide a range of total possible/estimated costs as it is unclear if the acquisition of the resource can be successful for various reasons. An item mentioned above corresponds to an element associated with a customized total care plan and total care plan templates.

It allows the purchaser/user to review the range of estimated costs based on different ways of acquiring the item, including but not limited to: if the item is new or used, with special discount, from a different brand or manufacturer, from a different seller, with different level of quality. Then the method further allows the purchaser to fine tune the care package list based on their preferences, and their budget for each item.

After the tuning is completed, it will create the final customized care package content with the specific preferences: used/new, quality, brand, manufacturer, etc. Both the content list and the preference will be stored in the database for future references and periodic acquisition.

The content list and the purchaser's preferences can be updated at any time, as well as the purchaser's budget level. The method can re-compute and produce another package content list as another curated care product package and reside in the database. The ability is provided for the user to retrieve different versions of the care package list that is associated with the same care plan just in case say the preferences have changed. This allows them to decide in real time which is the one to acquire if multiple ones are below their budget. This is what we call optimization over the preference because it is not necessary to choose the cheapest package.

At any point in time, the solution provides the option to have the system automatically re-compute and produce another package content list when there are cost changes made by seller and achieve the goal of getting the minimal cost while meeting purchaser's preference, budget requirement, and changing standard for the quality of the care for future acquisition.

A total care plan contains the details associated with the care plan's consumption rate of the package content. With this information, the optimization method also provides an option to automatically generate re-purchase order so care plan execution will not be affected by the unavailability of products when in need. The system can prompt the user to re-order earlier if the pricing was better than the usual price and the system will remember not to auto-reorder until the package is totally consumed. This is what we call optimization over the cost. Automatic re-purchasing the package contents is complemented by the purchaser deciding to manually re-purchase so to use other possible cost-cutting methods the system provides: conducting swapping transaction or system-wide group purchase discount. This is what we call optimization over special events.

A swapping transaction is implemented for purchasers and individual member sellers to purchase an item while paying for the purchase with another item. The method of enabling members to conduct swapping transactions is through utilizing the knowledge base of the total care plan management module 10. It analyzes the care plans, the care package items associated with each plan, and the period of time one item might be of use to the plan or in use by the plan, and produces a list of items that can be time-shared while the user is carrying out the care plan. These items are potential items that can be used for swapping transactions, and the users of these total care plans that use these items are potential acquirers of these items.

The system has a system-wide group purchase profile. When the system is made aware of external vendors are having special volume discount, it will analyze the care plans database for potential care plans and their owners who can benefit from each particular external volume discount to create purchasing groups with purchasers who are adopting the same care plan or similar care plans that use the volume discounted care package items.

The system implements a notification mechanism for users to be made aware of special events including when there are opportunities for using swapping, or joining other purchasers for volume discount to further reduce their total costs. Once the user member manually repurchases, the system will re-calculate the date when the regular re-order needs.

Now referring to FIG. 2 once more, a user logs into the system server 5 (which can be referred as the CareXc system server) via his/her computer 1. The system server 5 comprises a total care plan management module 10, a user and team management module 20, a care resources management module 30 and a marketplace management module 40. The system server 5 accesses, updates and makes queries to multiple databases such as total care plan database 60, users database 70, care resources database 80 and marketplace database 90 to provide the function of letting users customize a "total care plan". The system server 5 also access external websites 100 via internet so any information that may help in reducing the costs or increasing product availability can be monitored.

Figure 3:
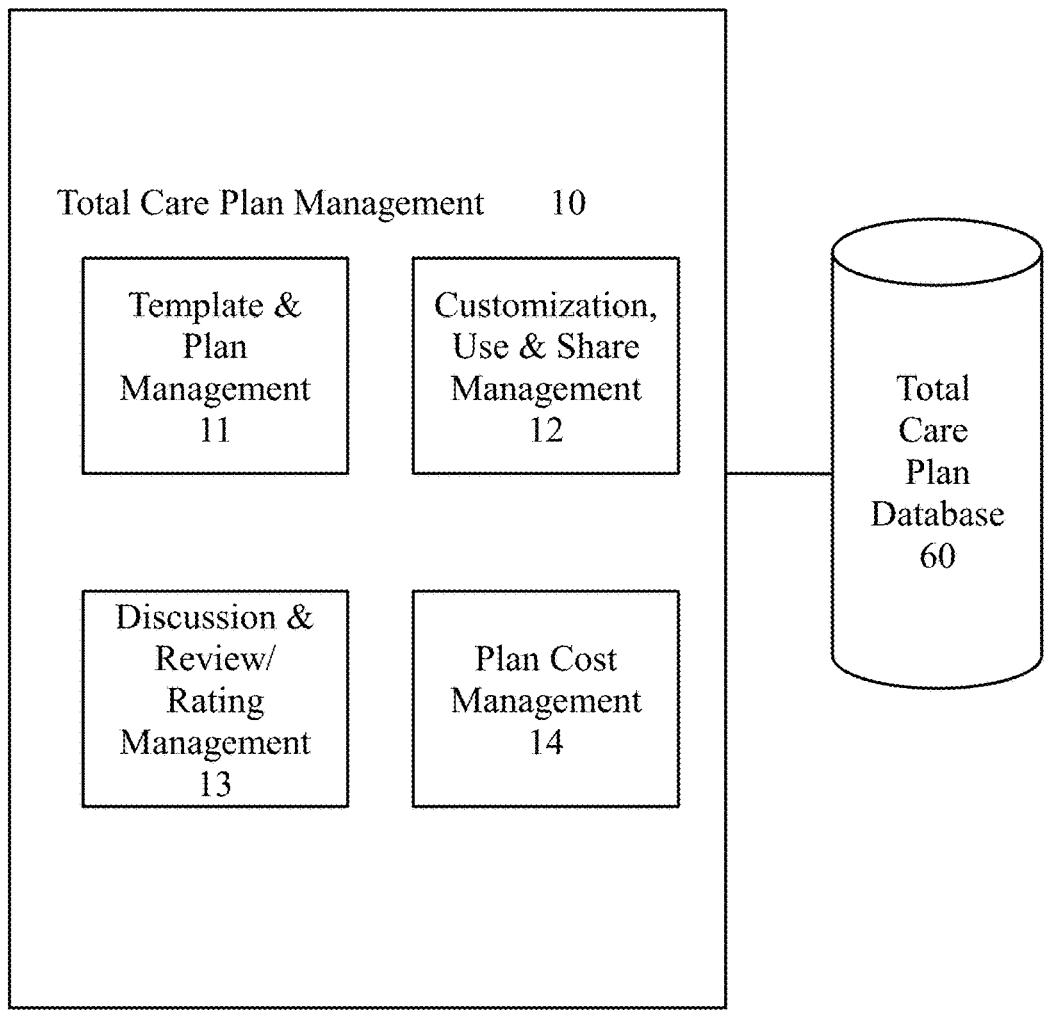
FIG. 3 illustrates the process flow and the components of the total care plan management module.

In FIG. 3, the components of the total care plan management module 10 are shown. The total care plan management module 10 comprises of a template and plan management submodule 11, a customization, use and share management submodule 12, a discussion and review/rating management submodule 13 and a plan cost management submodule 14. The template and plan management submodule 11 is responsible for integrating and managing the information curated from other caregivers who have caregiving experience on similar health conditions, generating and displaying the graphical representation of the total care plan template stored in the total care plan database 60 when the user wants to view a selected template. The customization, use and share management submodule 12 manages the customizations the user has made to the total care plan. After a customized total care plan is defined by the user, the customized total care plan is saved and stored in this user's private storage area of the total care plan database 60. If the user is willing to share this customized plan with others, a system administrator will review and approve the customized care plan as a total care plan template to be viewed as a curated plan in the system for sharing with other users with similar health problems.

The discussion and review/rating submodule 13 records the feedback from the users such as discussions, reviews and rating for the care plan template on the discussion interface and generates reports on the feedback for the template.

The plan cost management submodule 14 manages the costs of the care plan templates and customized plans. When there is a variation hourly rate for carrying out the care plan tasks or price in consumable products or medications detected, the plan cost management submodule 14 updates the price for the care plan templates. The cost of the customized total care plans can be optimized by the user delete the tasks, change team members or product resources in the adopted total care plan and decide if they want to use the new customized care plan as the plan to carry out the caregiving or change their financial constraint or quality goal.

Figure 4:
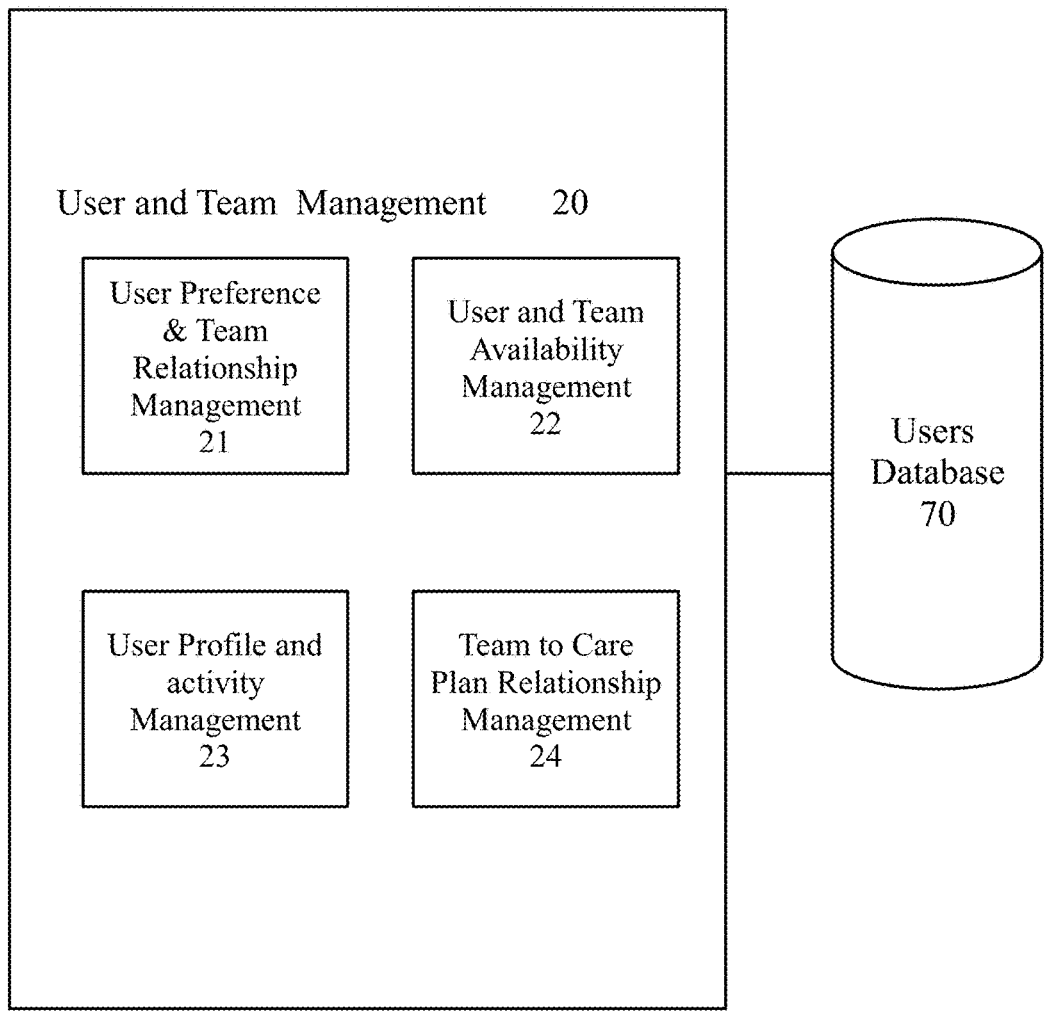
FIG. 4 illustrates the process flow and the components of the user and team management module.

In FIG. 4, the components of the user and team management module 20 are shown. The user and team management module 20 comprises user preferences and relationship management submodule 21, user availability management submodule 22, user profile and activity management submodule 23 and team to care plan submodule 24. User and team management module 20 accesses, manages, makes queries and updates the users database 70. The users database 70 stores the user accounts. Each user account comprises user specific information such as user preferences, user's health conditions, user's financial condition, the insurance carried, user activities, user availabilities, and user identity related information. The user identity related information comprises user's name, physical address, email address, phone number, birthday, login name, password, relationships between users.

A user may be a team member to carry out the services listed in the total care plan for other users in the users database 70. The user preferences and relationship management submodule 21 manages the preferences set by the users and manages the relationships between the users. E.g. User one is the care recipient of a total care plan, user two is an experienced physiotherapist and user three is a family member of user one's friend and is carrying out care routines similar to user one's care plan has for the other patients. Since user three might be able to provide services for patients with similar to user one's care routines, user three might become user one's caregiver too because user one's preference is to have friends or people with more experience as her caregivers. The user two might be the physiotherapist for user one because the care plan of user one has tasks that requires a physiotherapist. The relationships between users one to three are managed by the user preferences and relationship management submodule 21.

The user availability submodule 22 checks the availability of the time slots when a user may be able to provide services. E.g. User one needs someone to take the patient to the park with the dog during 5 pm to 6 pm every day. User two registers his/her availability to offer dog walking service at Saturday from 3 pm to 6 pm. The user availability submodule 22 manages and updates the availability for tasks or services of the users and displays the availability in a calendar view for users to easily see who may be available to help.

The user profile and activity submodule 23 manages each user's profile as it is the key database where the information of the users, their availability, their preferences, financial profile and the insurance status are all there for optimizing the cost of a plan. The user activity function is about how active they are in using the system and collects activity data when using the system. This information can be tremendously useful for many reasons: for example they may get system special discount to reward their frequent use of the system, the system helps the user remember the history of using the system, and use the data for monitoring the health conditions for further customizing the plan. The cost of the total care plans can be optimized by resetting the user's financial profile or the insurances carried as the preferred option in calculating the optimized costs.

Figure 5:
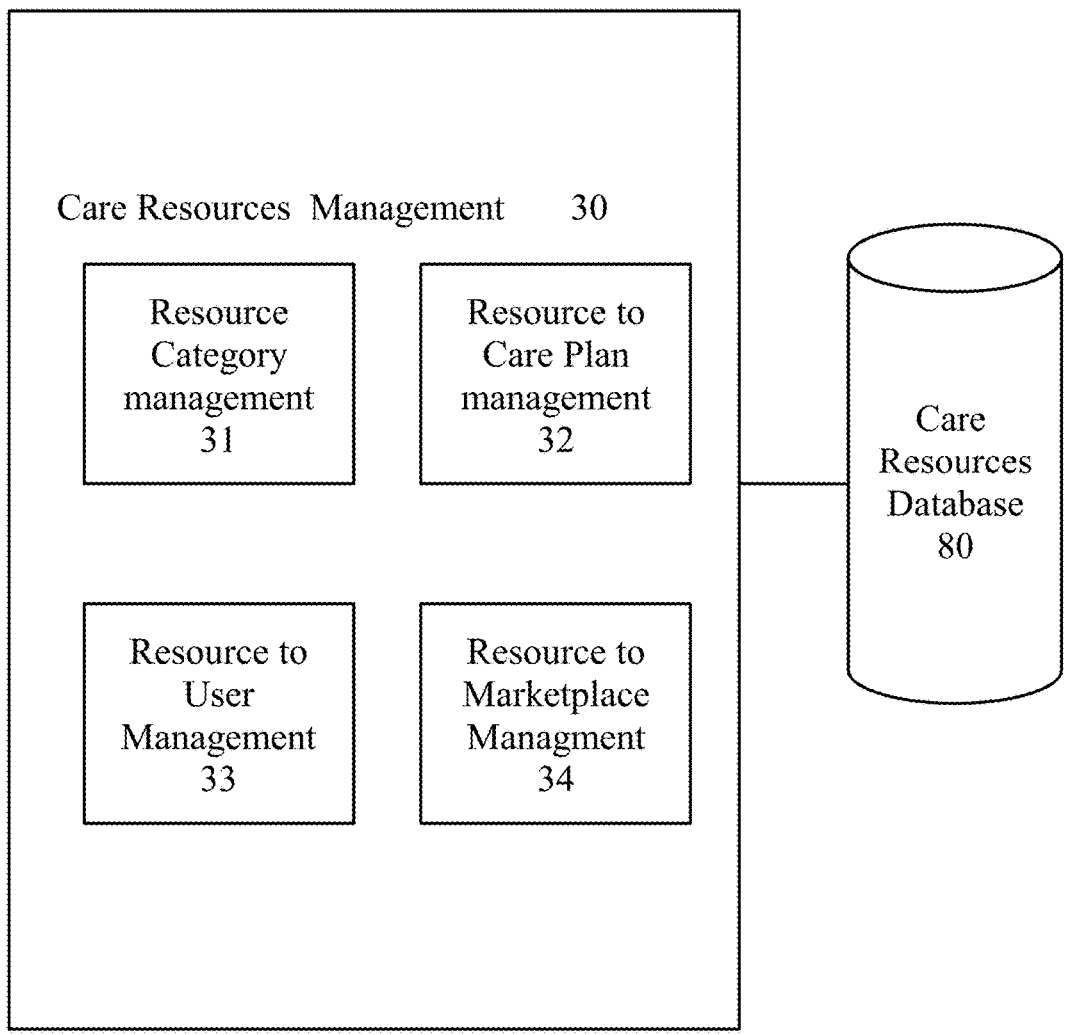
FIG. 5 illustrates the process flow and the components of the care resources management module.

The team to care plan submodule 24 provides management functions for finding and administering team members from the users in the users database 70 who have relationships or are professional caregivers who are looking for jobs for a team to carry out a user's customized total care plan. In FIG. 5, the components of the care resources management module 30 are shown. The care resources management module 30 comprises a resource category management submodule 31, a resource to care plan management submodule 32, a resource to user management submodule 33 and a resource to marketplace management submodule 34. The care resources management module 30 manages all care resources properties included in the stored total care plans and monitors whether a change has been made to the care resources in a care resources database 80, if there is any change made related to the use of the resources to the customized total care plan, user preferences associated with the customized total care plan, care packages associated with the customized total care plan or the resources or their properties in the care resources database 80. A customized total care plan may have a number of care packages. E.g. care plan one may have three care packages. Care package one may be for summer time when it is hot so the medication required may be difference. Care package two may be for winter time when it is so cold so extra products or services may be needed. Care package three may be for spring or autumn when the weather is cool and involves for outdoor activities.

The resource category management submodule 31 defines the categories of the resources and allocates the resources needed in the total care plan to a category. As in-home care resource providers have a very wide selection of resources from medical related products such as pillbox to non-medical related products such as gloves. Depending on the vendor, the category this product might be listed under can vary. The gloves may be listed under the household cleaning category at a hardware store or it may be listed under toileting aid category in a drugstore. This module will manage the relationship between the resource and the categories that it may belong so to help users find and acquire the product through a particular vendor.

The resource to care plan management submodule 32 associates the resources with the customized total care plan. A total care plan always has a list of resources, while all the detailed information is resided in the care resources database 80, this module helps total care plan management module 10 to retrieve any important information such as the vendors for a particular resource when customizing the plan. This module also helps the care resources database 80 keep up-to-date information such as how many care plans are using a particular resource.

The resource to user management submodule 33 assigns the resources to the user. Resources are key components for carrying out a user's total care plan with user's preference. It is important for the user to learn the details of one particular resource in order to truly customize their plan. For example, their preference on the skin lotion is a particular brand when their skin was not as dry but when they age, skin fundamentally changed to drier and drier, the brand used to be the best for them may no longer be useful. With this module, the system can then suggest the user to use a different brand at appropriate time. The cost of the total care plans can be optimized by setting resources assigned to the user according to user's preferences such as the brand of the product, new or used, cost range, and payment methods as the preferred option in calculating the optimized costs.

The resource to marketplace management submodule 34 manages the timely and correct association of the resources one needs in the total care plan to the product section of the marketplace. This association is important because products are key components of the marketplace. For example: if users have some resources that are no longer in need and this module will help them put the products in marketplace so the excess resources can be exchanged or trade in a sharing pool. E.g. the push chair is not needed temporarily so the push chair is put into the sharing pool for other uses to borrow the chair until it is needed again.

Figure 6:
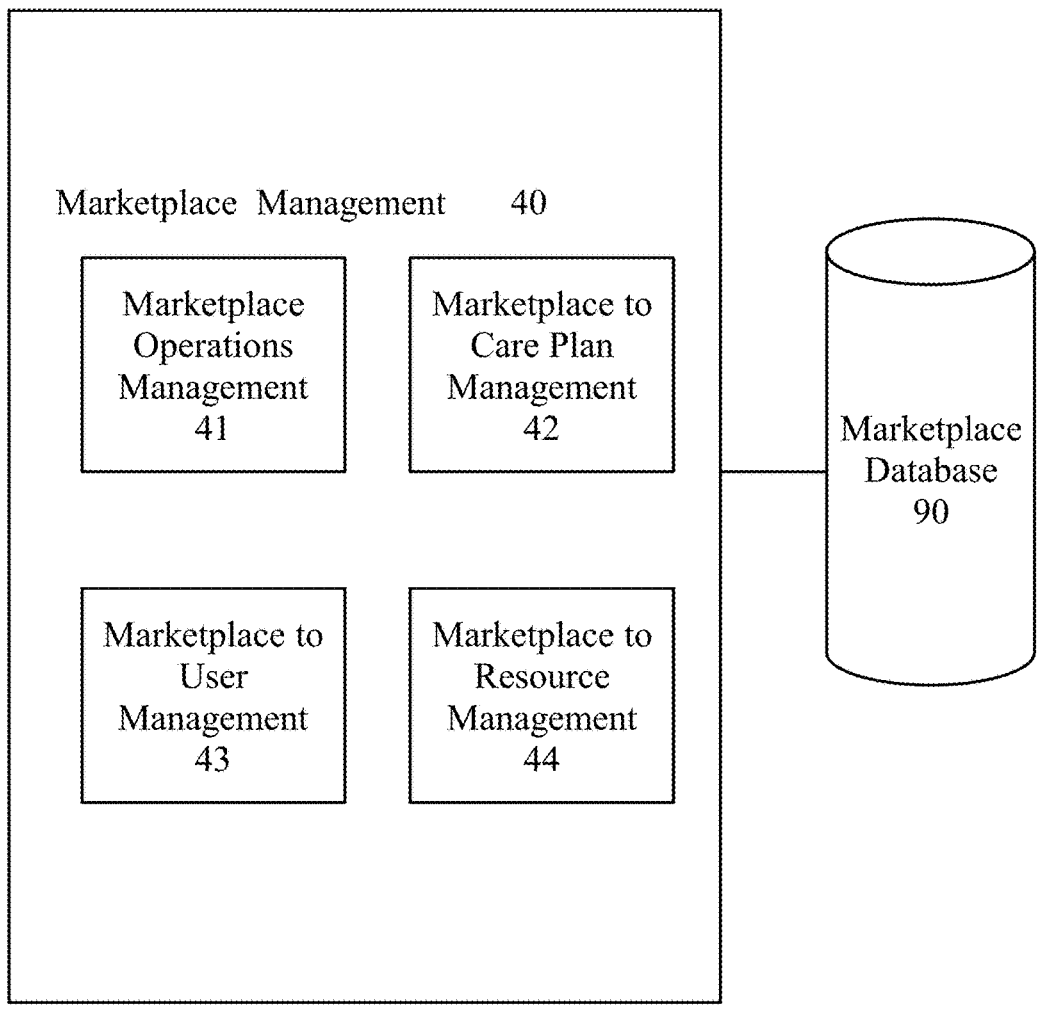
FIG. 6 illustrates the process flow and the marketplace management module.

In FIG. 6, the components of the marketplace management module 40 are shown. The marketplace management module 40 comprises a marketplace operations management submodule 41, a marketplace to care plan management submodule 42, a marketplace to user management submodule 43 and a marketplace to resource management submodule 44. The marketplace management module 40 manages the providers for the care resources; the exchanges took place in the sharing pool, the costs of the care packages. All the activities of the user using the marketplace are stored in the marketplace database 90. Information that may affect the costs of the customized total care plan and total care plan templates from external websites 100 are monitored and updated regularly to obtain the correct latest information for all customized total care plan and total care plan templates.

The marketplace operations management submodule 41 manages the operations took place in the marketplace. E.g. If there is a bulk buy discount for the goods used in the care plan detected from the external websites 100, the marketplace operation management module 41 notifies the user about this discount and groups the users who use same goods together to place the order to take the advantages of bulk buying discounts. E.g. If user one offers a service to walk a dog for an hour in exchange for two bags of adult diapers and user two requests for someone to walk the dog for one bag of adult diaper. The marketplace operation management submodule 41 may inform user one to send request to take the task from user two and negotiate for more bags of adult diaper or schedule for additional days to exchange for more bags of diapers. Thus the total costs of the total care plans for user one and two can be reduced and optimized. E.g. associating the profile of the user with social welfare programs or insurance programs that the user is qualified for and closely monitors the external insurance benefits websites and social program benefit websites to help the user learn the benefit him/her entitles so the user can apply for the aid he/she needs without having to pay the total cost for it.

The resource to care plan management submodule 42 informs the total care plan management module 10 that the resources have been changed so the total cost of the care plan can be updated automatically in the user interface screen.

The marketplace to user management submodule 43 informs the user and team management module 20 the relationship changes of the user who requests for help and the user who provides help as a caregiver so that the detail of the caregiving team can be updated. For example, user1 is looking for caregivers in the system, and when user2 has become available as a caregiver under some time slots. Both user1 and user2 will be in the marketplace database 90 but with one as a potential "buyer" while the other as a potential "seller". When the user and team management module 20 gets the notification from marketplace management module 40, it will notify user1 and user2 via email or phone or text message, whichever is their preference for them to work out the details directly for user2 to join user1's team.

The marketplace to resource management submodule 44 informs the care resources management module 30 about the changes in care resources (such as limited period of product discount) and the latest detail of the resources gathered from external and internal vendors so the care resources management module 30 can updates the care resources database 80 with the latest information. When the marketplace management module 40 recalculates the costs of the care plans, the updated information can be accessed from the care resources database 80 and sent to the total care plan management module 10.

The resource management module 30 contains the details about the quantity of each product needed by a care plan for a fixed period of time, say one month, and it keeps a count on the current quantity reduction from the execution of the care plan or user sold off or exchanged out some quantity of the product. The consumption period will also be reduced if the count is lower than it originally planned for. At the end of the period, an alarm will trigger the resource management module 30 to notify resource to marketplace module 34 to reorder the products. After the reorder is fulfilled, the quantity count is reset and the same monitoring process continues.

The server system 5 also provides the flexibility for the users to manually set one of the three optimization options as the prioritized option or automatically calculate the utmost optimized costs out of all the optimization options.

This invention creates a system that uniquely helps users understand the cost of an in-home care and can manually adjust the components of the plan cost to customize the plan to fit their quality and cost requirements. It then can systematically inform the users that the cost might have been different because of the market condition (new vendors with cheaper price, brand changes, etc.) or the care recipient's health condition has changed. It also will auto-reorder if the cost has not changed automatically without users having to remember to reorder.

These functions allows the family caregivers to reduce the extra time they have to spend in caring for their loved ones, have a desirable quality of care that they can afford, and improve the family caregiver's quality of life by reducing their stress in caregiving requirements.

Now that embodiments of the present invention have been shown and described in detail, various modifications and improvements thereon will become readily apparent to those skilled in the art. Accordingly, the spirit and scope of the present invention is to be construed broadly not limited by the foregoing specification.

What is claimed is:

1. A system for optimizing costs of and conducting purchasing of products and services based on care plans, the system displaying a one-stop-shop view of a total care plan template including details associated with a consumption rate and the system comprising a system server including:
    a total care plan management module being a first code segment for defining, generating and displaying a graphical representation of the total care plan template including the details, providing a plurality of care plan templates for a user to define at least one customized total care plan, monitoring a current consumption rate, and storing the plurality of care plan templates and the at least one customized total care plan in a total care plan database;
    a user and team management module being a second code segment for managing a plurality of user accounts in a users database, wherein the plurality of user accounts comprises a user specific information with a plurality of user preferences, a plurality of health conditions, a financial condition, insurances carried and a user identity related information stored in the users database;
    a care resources management module being a third code segment for managing a care resources database, the care resources database storing a plurality of care resources, each care resource having its properties, and the care resources management module monitoring whether a change has been made to the plurality of care resources, a change has been made related to the use of the plurality of care resources in the at least one customized total care plan, a change has been made in the plurality of user preferences, a change has been made to a plurality of care packages associated with the at least one customized total care plan, and a change has been made to the plurality of care resources including their properties, wherein the plurality of care packages are defined as all the care resources required for carrying out the at least one customized total care plan; and
    a marketplace management module being a fourth code segment for managing a plurality of providers of the care resources stored in the care resources database, the plurality of care packages needed, the cost of the plurality of care packages that can be afforded by the user and a plurality of available care packages according to the at least one customized total care plan, and for the user to make activities to access, wherein all the activities accessing the marketplace management module are stored in a marketplace database;
    wherein the care resources management module notifies the marketplace management module when the care resources management module detects a change has been made to the plurality of care packages associated with the user so the marketplace management module accesses a plurality of external websites for retrieving a latest information to optimize the total costs and the available care resources according to the plurality of user preferences, to notify the user and to conduct purchasing of the products and services.

2. The system of claim 1, wherein the total care plan management module further provides a curator interface allowing a system administrator to review and curate the customized total care plan into a curated total care plan template.

3. The system of claim 2, wherein the curated total care plan template is stored and added to the plurality of care plan templates, and allowed to be shared with other users.

4. The system of claim 3, wherein the user identity related information comprises at least one of a physical address, an email address, a phone number, a birthday, a login name, a password and relationships between users.

5. The system of claim 2, wherein the total care plan management module further provides a service registration function allowing a plurality of users to provide a list of available services or excess resources and a list of services or resources needed.

6. The system of claim 5, wherein the user and team management module further assigns a service providing user to a service-needing user as a care plan service providing team member of the service-needing user.

7. The system of claim 5, wherein the marketplace management module regularly monitors the plurality of external websites, a plurality of external systems, and the list of excess resources in the system to provide an information for automatically updating the total costs for each of the care plan templates and the at least one customized total care plan, matches at least one available service or excess resource in the list of available services or excess resources with at least one service or resource in the list of services or resources needed between the plurality of users, and generates a plurality of suggestion messages to notify a plurality of matched users.

8. The system of claim 7, wherein the marketplace module further provides a notification message to the users about a possible change in the total costs by monitoring a plurality of social welfare programs and a plurality of insurance programs that the users are qualified for as listed in a plurality of the users' profiles.

9. The system of claim 5, wherein the care resources management module further monitors a list of available resources associated with the at least one customized total care plan, when an available resource in the list of available resources is redundant, the care resources management module prompts the user to register the available resource into a sharing pool so the available resource can be re-sold or exchanged for other available resources in the sharing pool.

10. A computer-implemented method for optimizing a cost based on a care plan and conducting an exchange among services and products, comprising:
providing a plurality of total care plan templates using a system server, wherein the system server defines, generates and displays a graphical representation of the total care plan template including details;
allowing users to visually view the details including resource needs of the plurality of total care plan templates;
defining and generating at least one customized total care plan visually using at least one total care plan template from the plurality of total care plan templates;
managing a plurality of user accounts in a database, wherein the plurality of user accounts comprises a user specific information including a plurality of user preferences;
monitoring whether a change has been made to the at least one customized total care plan;
managing a total estimated cost and a plurality of available resources according to the at least one customized total care plan;
obtaining a list of available services and excess resources from users;
updating a list of needed services and resources from the users; and
matching at least one in the list of available services and excess resources with at least one in the list of needed services and resources,
wherein when a change has been made to the at least one customized total care plan, a latest information is retrieved from a plurality of external websites and, the plurality of available resources, and a sharing pool of excessive resources to optimize the cost of each customized total care plan that is impacted according to the plurality of user preferences and a result from matching at least one in the list of available services and excess resources with at least one in the list of needed services and resources to notify the users and to conduct the exchange among services and products.

11. The computer-implemented method of claim 10, further comprising:
providing a curator interface for a system administrator to review and curate the customized total care plan into a curated total care plan template.

12. The computer-implemented method of claim 11, further comprising:
storing the curated total care plan template;
appending the curated total care plan to a set of the plurality of other total care plan templates that the users can view; and
sharing the curated total care plan with other users.

13. The computer-implemented method of claim 12, further comprising:
providing a service registration function;
generating a plurality of suggestion messages;
notifying the matched users for possible exchanges or acquisitions; and
assigning a user who had agreements to provide services with the matched at least one in the list of needed services and resources as a care plan team member of the matched at least one user in the list of needed services and resources.

14. The computer-implemented method of claim 13, further comprising:
monitoring the plurality of external websites and a plurality of external systems regularly for price changes; and
updating the total estimated costs for each of the plurality of total care plan templates and every customized total care plan automatically when a price of an element associated with the customized total care plan and the plurality of total care plan templates changed.

15. The computer-implemented method of claim 14, further comprising:
associating a profile of a user with social welfare programs or insurance programs that the user is qualified for; and
monitoring a plurality of external insurance benefits websites and a plurality of social program benefit websites for reducing the cost of the at least one customized total care plan.

16. The computer-implemented method of claim 15, further comprising:
monitoring a list of available resources associated with the at least one customized total care plan for a user; and
when an available resource in the list of available resources is redundant, prompting the user to register the available resource into a sharing pool.

17. The computer-implemented method of claim 16, further comprising:
monitoring consumption levels of consumables associated with the at least one customized total care plan for the user;
providing options for automatically placing orders or prompting the user to place orders for the consumables; and
providing a negotiation interface allowing a plurality of users to negotiate for selling and purchasing the consumables.

18. The computer-implemented method of claim 17, further comprising:
matching the users that use the same consumables;

sending requests to the matched users to obtain authorizations for joining orders for volume discounts;
receiving the authorizations from the matched users;
re-calculating the cost of each customized total care plan that benefits from the volume discounts; and
placing the joining orders for the matched users.

19. The computer-implemented method of claim 18, wherein the user specific information further includes a plurality of user identity related information comprising at least one of a physical address, an email address, a phone number, a birthday, a login name, a password and relationships between the users.

20. A computer-implemented method for optimizing a cost of and conducting purchasing of products and services based on a care plan, comprising:
providing a plurality of total care plan templates using a system server, wherein the system server defines, generates and displays a graphical representation of the total care plan template including details;
allowing users to visually view the details including resource needs of the plurality of total care plan templates;
defining at least one customized total care plan visually using at least one total care plan template from the plurality of total care plan templates;
managing a plurality of user accounts in a database, wherein the plurality of user accounts comprises a user specific information including a plurality of user preferences;
monitoring whether a change has been made to the at least one customized total care plan;
managing a total estimated cost and a plurality of available resources according to the at least one customized total care plan;
providing a curator interface for a system administrator to review and curate the customized total care plan into a curated total care plan template;
storing the curated total care plan template;
appending the curated total care plan to a set of the plurality of other total care plan templates that users can view;
sharing the curated total care plan with other users; and
purchasing the products and services according to the at least one customized total care plan,
wherein when a change has been made to the at least one customized total care plan, a latest information is retrieved from a plurality of external websites and the plurality of available resources to optimize the cost of each customized total care plan that is impacted according to the plurality of user preferences and to notify the users.

* * * * *